(12) United States Patent
Koga

(10) Patent No.: US 11,717,205 B2
(45) Date of Patent: Aug. 8, 2023

(54) SHOVEL, ASSIST DEVICE FOR SHOVEL, AND MANAGEMENT APPARATUS FOR SHOVEL

(71) Applicant: SUMITOMO HEAVY INDUSTRIES, LTD., Tokyo (JP)

(72) Inventor: Masato Koga, Kanagawa (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 477 days.

(21) Appl. No.: 16/782,459

(22) Filed: Feb. 5, 2020

(65) Prior Publication Data

US 2020/0170561 A1 Jun. 4, 2020

Related U.S. Application Data

(63) Continuation of application No. PCT/JP2018/029356, filed on Aug. 6, 2018.

(30) Foreign Application Priority Data

Aug. 8, 2017 (JP) .................................. 2017-153670

(51) Int. Cl.
*A61B 5/18* (2006.01)
*A61B 5/00* (2006.01)
*B60K 28/06* (2006.01)
*B60N 2/00* (2006.01)
*E02F 9/26* (2006.01)
*E02F 3/32* (2006.01)

(52) U.S. Cl.
CPC .............. *A61B 5/18* (2013.01); *A61B 5/6887* (2013.01); *A61B 5/7246* (2013.01); *B60K 28/06* (2013.01); *B60N 2/002* (2013.01); *E02F 9/26* (2013.01); *A61B 2503/22* (2013.01); *E02F 3/32* (2013.01)

(58) Field of Classification Search
USPC .......... 180/271–273; 340/540–541; 280/735; 600/300–301
See application file for complete search history.

(56) References Cited

U.S. PATENT DOCUMENTS 5,931,254 A * 8/1999 Loraas ...................... E02F 9/24
180/272
5,999,872 A 12/1999 Kinugawa et al.
(Continued)

FOREIGN PATENT DOCUMENTS

EP 2878263 6/2015
JP H10-060948 3/1998
(Continued)

OTHER PUBLICATIONS

International Search Report for PCT/JP2018/029356 dated Oct. 2, 2018.

*Primary Examiner* — Shirley X Jian
(74) *Attorney, Agent, or Firm* — IPUSA, PLLC

(57) ABSTRACT

A shovel includes a lower traveling body, an upper turning body turnably mounted on the lower traveling body, a cab mounted on the upper turning body, an operating information obtaining device configured to obtain operating information, and a processor configured to store the operating information. The processor is configured to obtain the biological information of an operator in the cab and to correlate the biological information and the operating information.

19 Claims, 9 Drawing Sheets

(56) References Cited

U.S. PATENT DOCUMENTS

| | | | |
|---|---|---|---|
| 6,575,902 B1* | 6/2003 | Burton | G08B 21/06 600/595 |
| 6,927,694 B1* | 8/2005 | Smith | B60K 28/066 340/576 |
| 7,164,117 B2* | 1/2007 | Breed | B60R 21/0152 250/221 |
| 7,575,248 B2* | 8/2009 | Breed | B60R 21/01536 701/45 |
| 9,020,697 B2* | 4/2015 | Ricci | G06F 9/451 701/36 |
| 9,721,474 B2* | 8/2017 | Eskilson | A61B 5/18 |
| 9,809,115 B2* | 11/2017 | Mäder | G08B 21/06 |
| 10,315,662 B2* | 6/2019 | Terwilliger | B60W 50/0098 |
| 10,391,940 B2* | 8/2019 | Izumikawa | E02F 9/261 |
| 10,723,226 B1* | 7/2020 | Heitsman | G06V 40/10 |
| 11,161,410 B2* | 11/2021 | Heitsman | B60K 28/066 |
| 11,377,825 B2* | 7/2022 | Koga | E02F 3/435 |
| 2002/0161501 A1* | 10/2002 | Dulin | B60H 1/00742 701/45 |
| 2007/0203630 A1 | 8/2007 | Vitale et al. | |
| 2012/0296574 A1* | 11/2012 | Ooki | E02F 9/2095 702/35 |
| 2014/0172467 A1* | 6/2014 | He | A61B 5/18 705/4 |
| 2014/0297160 A1* | 10/2014 | Magaki | E02F 9/26 701/103 |
| 2014/0310739 A1* | 10/2014 | Ricci | G06F 21/31 725/75 |
| 2015/0114731 A1* | 4/2015 | Tsukamoto | E02F 9/16 180/53.8 |
| 2015/0135695 A1* | 5/2015 | Thekanath | E02F 9/26 60/420 |
| 2017/0113664 A1* | 4/2017 | Nix | B60T 8/241 |
| 2017/0309089 A1 | 10/2017 | Shimada et al. | |
| 2018/0143625 A1* | 5/2018 | Nelson | E02F 9/26 |
| 2018/0215395 A1* | 8/2018 | Keany | B60W 50/14 |
| 2018/0222390 A1* | 8/2018 | Imaizumi | E02F 9/0841 |
| 2020/0080851 A1* | 3/2020 | Edwards | G01C 21/3407 |
| 2022/0042282 A1* | 2/2022 | Nakayama | E02F 9/26 |
| 2022/0074171 A1* | 3/2022 | Izumikawa | G06T 7/521 |

FOREIGN PATENT DOCUMENTS

| | | |
|---|---|---|
| JP | 2003-058742 | 2/2003 |
| JP | 2008-056023 | 3/2008 |
| JP | 2010-111292 | 5/2010 |
| JP | 2011-038346 | 2/2011 |
| JP | 2012-030696 | 2/2012 |
| JP | 2015-071318 | 4/2015 |
| JP | 2016-018314 | 2/2016 |
| JP | 2016-88497 | 5/2016 |
| JP | 2016-133849 | 7/2016 |
| JP | 2016-186812 | 10/2016 |
| JP | 2017-065428 | 4/2017 |

\* cited by examiner

SHOVEL, ASSIST DEVICE FOR SHOVEL, AND MANAGEMENT APPARATUS FOR SHOVEL

CROSS-REFERENCE TO RELATED APPLICATIONS

This application is a continuation application filed under 35 U.S.C. 111(a) claiming benefit under 35 U.S.C. 120 and 365(c) of PCT International Application No. PCT/JP2018/029356, filed on Aug. 6, 2018 and designating the U.S., which claims priority to Japanese patent application No. 2017-153670, filed on Aug. 8, 2017. The entire contents of the foregoing applications are incorporated herein by reference.

BACKGROUND

Technical Field

The present invention relates to shovels, assist devices for shovels, and management apparatuses for shovels.

Description of Related Art

A shovel including an operation assist system that calculates the level of fatigue of its operator by multiplying the total time of turning operation, the total time of traveling operation, and the total time of excavation operation by respective predetermined weighting factors is known. This shovel notifies the operator that the operator is tired when the calculated level of fatigue exceeds a predetermined threshold.

SUMMARY

According to an aspect of the present invention, a shovel includes a lower traveling body, an upper turning body turnably mounted on the lower traveling body, a cab mounted on the upper turning body, an operating information obtaining device configured to obtain operating information, and a processor configured to store the operating information. The processor is configured to obtain the biological information of an operator in the cab and to correlate the biological information and the operating information.

DETAILED DESCRIPTION

The above-described shovel, however, merely estimates the level of fatigue of the operator based on various operating times, and the estimation may be inaccurate. This is because the level of fatigue of the operator differs greatly depending on a work environment. For example, even with the work contents and the work time being the same, the operator is more likely to become tired in the case of performing work under direct sunlight than in the case of performing work without exposure to sunlight.

Therefore, it is desired to enable more accurate estimation of the level of fatigue of the operator.

According to an aspect of the present invention, a shovel that enables more accurate estimation of the level of fatigue of its operator is provided.

Figure 1:
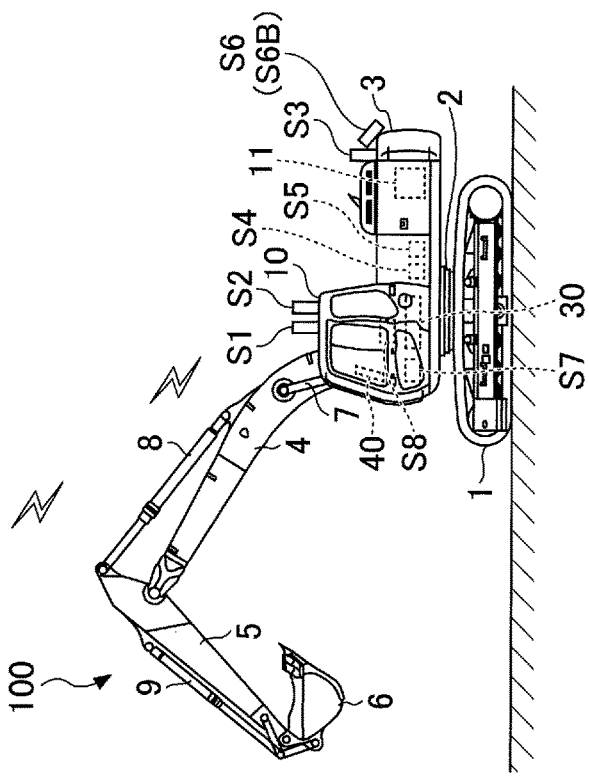
FIG. 1 is a schematic diagram illustrating an example configuration of a health management system.
Figure 2:
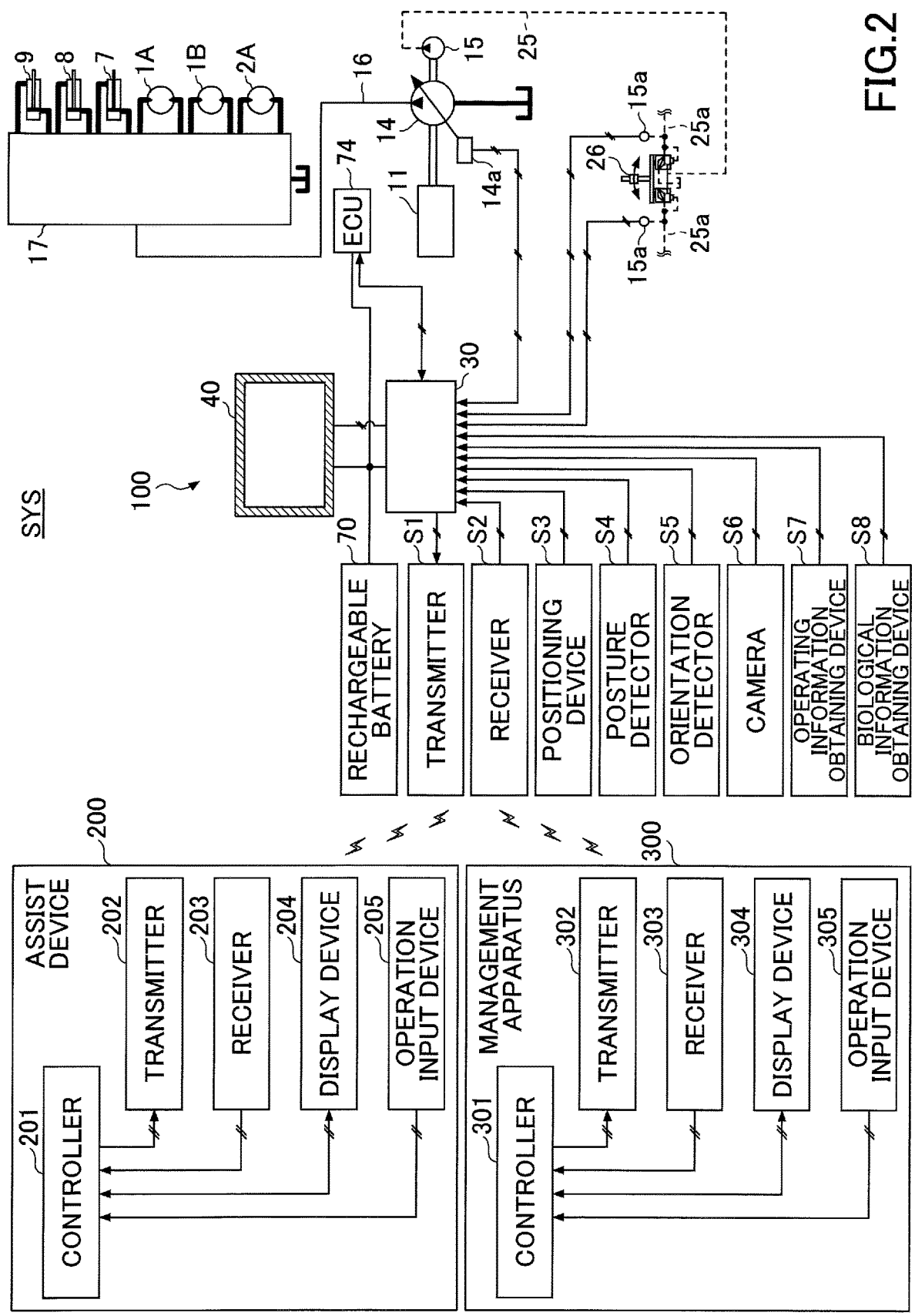
FIG. 2 is a diagram of a system configuration of the health management system.
Figure 3:
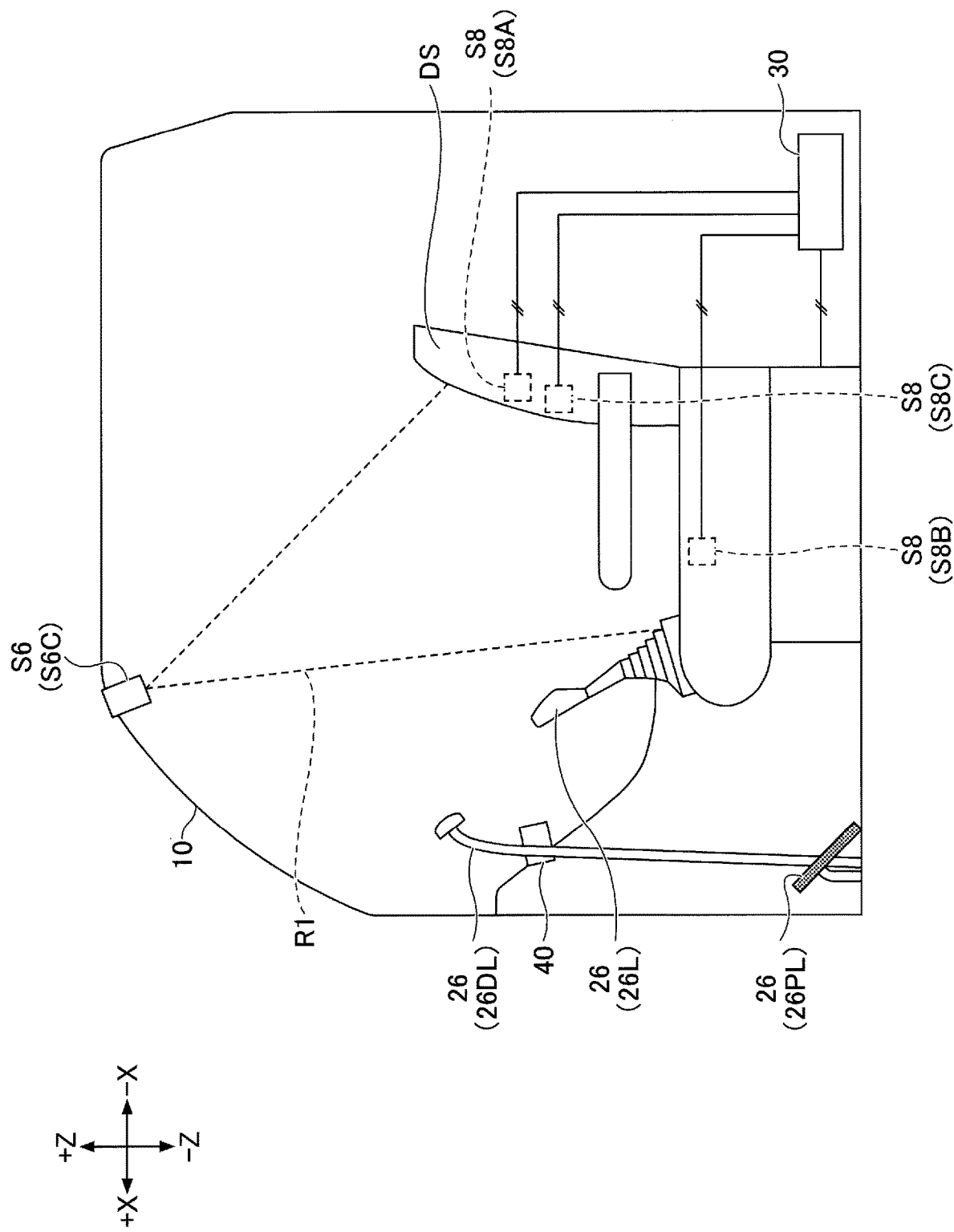
FIG. 3 is a side view of the inside of a cabin.

First, a health management system SYS including a shovel (excavator) according to an embodiment of the present invention is described with reference to FIGS. 1 through 3. FIG. 1 is a schematic diagram illustrating an example configuration of the health management system SYS. FIG. 2 is a diagram of a system configuration of the health management system SYS. FIG. 3 is a left side view of the inside of a cabin 10.

The health management system SYS is a system to manage the heath of a shovel operator. According to this embodiment, the health management system SYS is a system to manage the fatigue of a shovel operator, and mainly includes a shovel 100, an assist device 200, and a management apparatus 300. Each of the shovel 100, the assist device 200, and the management apparatus 300 constituting the health management system SYS may be one or more in number. According to this embodiment, the single shovel 100, the single assist device 200, and the single management apparatus 300 are included.

The assist device 200 is a portable terminal device, and is, for example, a computer carried by a worker or the like at a work site, such as a notebook PC, a tablet PC, or a smartphone. The assist device 200 may also be a computer carried by an operator of the shovel 100.

The management apparatus 300 is a stationary terminal apparatus, and is, for example, a computer installed in a management center or the like outside a work site. The management apparatus 300 may also be a portable computer (for example, a portable terminal device such as a notebook PC, a tablet PC, or a smartphone).

An upper turning body 3 is mounted on a lower traveling body 1 of the shovel 100 via a turning mechanism 2. A boom 4 is attached to the upper turning body 3. An arm 5 is attached to the end of the boom 4, and a bucket 6 is attached to the end of the aim 5. The boom 4, the arm 5, and the bucket 6 as work elements constitute an excavation attachment that is an example of an attachment. The boom 4, the arm 5, and the bucket 6 are hydraulically driven by a boom cylinder 7, an arm cylinder 8, and a bucket cylinder 9, respectively. A cabin 10 serving as a cab is provided on and a power source such as an engine 11 is mounted on the upper turning body 3.

As illustrated in FIG. 2, the shovel 100 includes the engine 11, a main pump 14, a pilot pump 15, a control valve 17, an operating apparatus 26, a controller 30, and an engine control unit (ECU) 74.

The engine 11 is a drive source of the shovel 100, and is, for example, a diesel engine that operates in such a manner as to maintain a predetermined rotational speed. The rotating shaft of the engine 11 is connected to the rotating shaft of each of the main pump 14 and the pilot pump 15.

The main pump 14 is a swash plate variable displacement hydraulic pump that supplies hydraulic oil to the control valve 17 via a hydraulic oil line 16. The discharge flow rate per revolution of the main pump 14 changes according as the swash plate tilt angle changes. The swash plate tilt angle is controlled by, for example, a regulator 14a. For example, the regulator 14a changes the swash plate tilt angle according as a control electric current from the controller 30 changes. A discharge pressure sensor to detect the discharge pressure of the main pump 14 and a tilt angle sensor to detect the swash plate tilt angle are attached to the shovel 100.

The pilot pump 15 is a fixed displacement hydraulic pump that supplies hydraulic oil to various hydraulic control apparatus such as the operating apparatus 26 via a pilot line 25.

The control valve 17 is a set of flow control valves that controls the flow of hydraulic oil with respect to hydraulic actuators. The control valve 17 selectively supplies hydraulic oil received from the main pump 14 through the hydraulic oil line 16 to one or more hydraulic actuators in accordance with a change in a pilot pressure commensurate with the direction of operation and the amount of operation of the operating apparatus 26. The hydraulic actuators include, for example, the boom cylinder 7, the arm cylinder 8, the bucket cylinder 9, a left traveling hydraulic motor 1A, a right traveling hydraulic motor 1B, and a turning hydraulic motor 2A. A hydraulic oil pressure sensor to detect the pressure of hydraulic oil in hydraulic actuators may be attached to the shovel 100.

The operating apparatus 26 is an apparatus that an operator of the shovel 100 uses to operate the hydraulic actuators. The operating apparatus 26 receives hydraulic oil supplied from the pilot pump 15 via the pilot line 25 to generate a pilot pressure, and causes the pilot pressure to act on a pilot port of a corresponding flow control valve through a pilot line 25a. The pilot pressure changes in accordance with the direction of operation and the amount of operation of the operating apparatus 26. A pilot pressure sensor 15a detects the pilot pressure, and outputs its detection value to the controller 30. FIG. 3 illustrates a left operating lever 26L, a left travel pedal 26PL, and a left travel lever 26DL that are constituents of the operating apparatus 26.

The controller 30 is a control device for controlling the shovel 100. According to this embodiment, the controller 30 is composed of a computer including a CPU, a volatile storage medium, and a non-volatile storage medium. The CPU of the controller 30 executes programs corresponding to various functions, thereby implementing the functions corresponding to the programs.

The engine control unit 74 is a device to control the engine 11. For example, the engine control unit 74 controls the amount of fuel injection, etc., so that an engine rotational speed set via an input device is achieved. An engine rotational speed sensor, an engine load factor sensor, a fuel injection amount sensor, etc., are connected to the engine control unit 74. The engine load factor sensor may be an engine torque sensor.

Each of a transmitter S1, a receiver S2, a positioning device S3, a posture detector S4, an orientation detector S5, a camera S6, an operating information obtaining device S7, a biological information obtaining device S8, and a display device 40 that are attached to the upper turning body 3 is connected to the controller 30. The controller 30 executes various operations based on the output information of each of the receiver S2, the positioning device S3, the posture detector S4, the orientation detector S5, the camera S6, the operating information obtaining device S7, and the biological information obtaining device S8. The controller 30 transmits information generated based on the operation results outside from the transmitter S1 or displays the information on the display device 40.

The transmitter S1 transmits information outside the shovel 100. For example, the transmitter S1 transmits information that can be received by at least one of the assist device 200 and the management apparatus 300 (hereinafter, "external apparatus"). According to the embodiment, the transmitter S1 transmits information that can be received by the external apparatus to the external apparatus through a satellite channel, a cellular phone line, or the like.

The receiver S2 receives information from outside the shovel 100. For example, the receiver S2 receives information transmitted by the external apparatus. According to this embodiment, the receiver S2 receives information transmitted by the external apparatus through a satellite channel, a cellular phone line, or the like.

The positioning device S3 obtains information related to the position of the shovel 100. According to this embodiment, the positioning device S3 is a GNSS (GPS) receiver, and measures the latitude, longitude, and altitude of a position at which the shovel 100 is present.

The posture detector S4 detects the attitude of the shovel 100. The attitude of the shovel 100 is, for example, the posture of the excavation attachment. According to this embodiment, the posture detector S4 includes a boom angle sensor, an arm angle sensor, a bucket angle sensor, and a body tilt sensor. The boom angle sensor is a sensor to obtain a boom angle. Examples of the boom angle sensor include a rotation angle sensor to detect the rotation angle of a boom foot pin, a stroke sensor to detect the stroke amount of the boom cylinder 7, and an inclination (acceleration) sensor to detect the inclination angle of the boom 4. The boom angle sensor may be a combination of an acceleration sensor and a gyro sensor. The same is true for the arm angle sensor and the bucket angle sensor. The body tilt sensor is a sensor to obtain a body tilt angle, and for example, detects the tilt angle of the upper turning body 3 relative to a horizontal plane. According to this embodiment, the body tilt sensor is a two-axis acceleration sensor that detects the tilt angle of the upper turning body 3 around its longitudinal axis and lateral axis. For example, the longitudinal axis and the lateral axis of the upper turning body 3 are perpendicular to each other and pass the shovel center point that is a point on the turning axis of the shovel 100. The body tilt sensor may also be a three-axis acceleration sensor.

The orientation detector S5 detects the orientation of the shovel 100. The orientation detector S5 is composed of, for example, a geomagnetic sensor, a resolver or encoder with respect to the turning axis of the turning mechanism 2, a gyro sensor, or the like. According to this embodiment, the orientation detector S5 is composed of a combination of a three-axis acceleration sensor and a gyro sensor. The orientation detector S5 may also be a pair of GNSS receivers.

The controller 30 can obtain information on the trajectory of the teeth tips of the bucket 6 based on the outputs of the positioning device S3, the posture detector S4, and the orientation detector S5.

The controller 30, the display device 40, the engine control unit 74, etc., are supplied with electric power from a rechargeable battery 70 to operate. The rechargeable battery 70 is charged by a generator driven by the engine 11. The electric power of the rechargeable battery 70 is also supplied to the starter of the engine 11, etc. The starter is driven with electric power from the rechargeable battery 70 to start the engine 11.

The camera S6 outputs an obtained image to the controller 30. According to this embodiment, the camera S6 includes a back camera S6B that captures an image of a space behind the shovel 100, and may include a right camera to capture an image of a space to the right of the shovel 100 and a left camera to capture an image of a space to the left of the shovel 100. The camera S6 further includes an indoor camera S6C that captures an image of the operator in the cabin 10. An area R1 indicated by a dashed line in FIG. 3 represents the imaging range of the indoor camera S6C. The controller 30 may identify or authenticate the operator by performing various kinds of image processing on the image of the operator captured by the indoor camera S6C.

The operating information obtaining device S7 obtains operating information that is information on the operation of the shovel 100. According to this embodiment, the operating information obtaining device S7 includes the pilot pressure sensor 15a, a discharge pressure sensor, a tilt angle sensor, a hydraulic oil pressure sensor, an engine rotational speed sensor, an engine load factor sensor, a fuel injection amount sensor, the positioning device S3, the posture detector S4, the orientation detector S5, etc. The operating information may include information on a work environment. In this case, the operating information obtaining device S7 may include an ambient temperature sensor, an inside temperature sensor, a barometric pressure sensor, a humidity sensor, an illuminance sensor, a body tilt sensor, a vibration sensor, etc.

The biological information obtaining device S8 obtains biological information that is information on the operator of the shovel 100. According to this embodiment, the biological information obtaining device S8 may include a pulse sensor S8A, a body pressure sensor S8B, and a body temperature sensor S8C buried in an operator seat DS, and may also include a scale buried in the operator seat DS. The biological information obtaining device S8 may be configured to repeatedly obtain the biological information of the operator at predetermined control intervals once the operator is seated in the operator seat DS.

The biological information obtaining device S8 may include the indoor camera S6C. In this case, the controller 30 may determine the physical condition of the operator by performing various kinds of image processing on the image of the operator captured by the indoor camera S6C.

The biological information obtaining device S8 may be a sensor worn by the operator (wearable sensor), such as a wrist wearable pulsimeter or a wrist wearable blood pressure gauge. The wearable sensor may be configured to output biological information together with wearing information. The wearing information is information indicating whether the operator is wearing a wearable sensor.

The operator seat DS is a seat in which a shovel operator sits. According to this embodiment, the operator seat DS is a massage chair that can operate in response to a control command from the controller 30. Specifically, the operator seat DS is configured such that its mode of operation can be selected. Modes of operation may be categorized according to massage techniques such as "kneading," "Shiatsu," "percussion," and "kneading and percussion," or may be categorized according to massaged parts such as "shoulders," "waist," "calves," and "thighs". The operator of the shovel 100 can use the massage function of the operator seat DS at any time. The massage function of the operator seat DS may be automatically controlled by the controller 30. The operator seat DS may be configured such that the massage function automatically starts when a predetermined condition is satisfied, for example.

The display device 40 is a device to display various kinds of information, and is placed near the operator seat DS in the cabin 10. According to this embodiment, the display device 40 can display an image captured by the camera S6. The image captured by the camera S6 may be a composite image obtained by combining images captured by multiple cameras. The composite image may be subjected to various kinds of image processing such as viewpoint changing. The display device 40 may be a portable terminal device such as a notebook PC, a tablet PC, or a smartphone.

The assist device 200 includes a controller 201, a transmitter 202, a receiver 203, a display device 204, and an operation input device 205.

The controller 201 is a device for controlling the assist device 200. According to this embodiment, the controller 201 is composed of a computer including a volatile storage medium and a non-volatile storage medium. The CPU of the controller 201 executes programs corresponding to various functions, thereby implementing the functions corresponding to the programs.

The transmitter 202 transmits information outside the assist device 200. For example, the transmitter 202 transmits information that can be received by at least one of the shovel 100 and the management apparatus 300 to the shovel 100 through a satellite channel, a cellular phone line, or the like.

The receiver 203 receives information from outside the assist device 200. For example, the receiver 203 receives information transmitted by at least one of the shovel 100 and the management apparatus 300 through a satellite channel, a cellular phone line, or the like.

The display device 204 is a device for displaying various kinds of information. According to this embodiment, the display device 204 is a liquid crystal display, and displays information on work by the shovel 100, information on the fatigue of the operator of the shovel 100, information on terrain data, etc.

The operation input device 205 is a device for receiving operation inputs. According to this embodiment, the operation input device 205 is a touchscreen placed on the liquid crystal display. The operation input device 205 may also be a touchpad, a keyboard, a mouse, a trackball, or the like.

The management apparatus 300 includes a controller 301, a transmitter 302, a receiver 303, a display device 304, and an operation input device 305.

The controller 301 is a device for controlling the management apparatus 300. According to this embodiment, the controller 301 is composed of a computer including a volatile storage medium and a non-volatile storage medium. The CPU of the controller 301 executes programs corresponding to various functions, thereby implementing the functions corresponding to the programs.

The transmitter 302 transmits information outside the management apparatus 300. For example, the transmitter 302 transmits information that can be received by at least one of the shovel 100 and the assist device 200 to the shovel 100 through a satellite channel, a cellular phone line, or the like.

The receiver 303 receives information from outside the management apparatus 300. For example, the receiver 303 receives information transmitted by at least one of the shovel 100 and the assist device 200 through a satellite channel, a cellular phone line, or the like.

The display device 304 is a device for displaying various kinds of information. According to this embodiment, the display device 304 is a liquid crystal display, and displays information on work by the shovel 100, information on the fatigue of the operator of the shovel 100, information on terrain data, etc.

The operation input device 305 is a device for receiving operation inputs. According to this embodiment, the operation input device 305 is a touchscreen placed on the liquid crystal display. The operation input device 305 may also be a touchpad, a keyboard, a mouse, a trackball, or the like.

Figure 4:
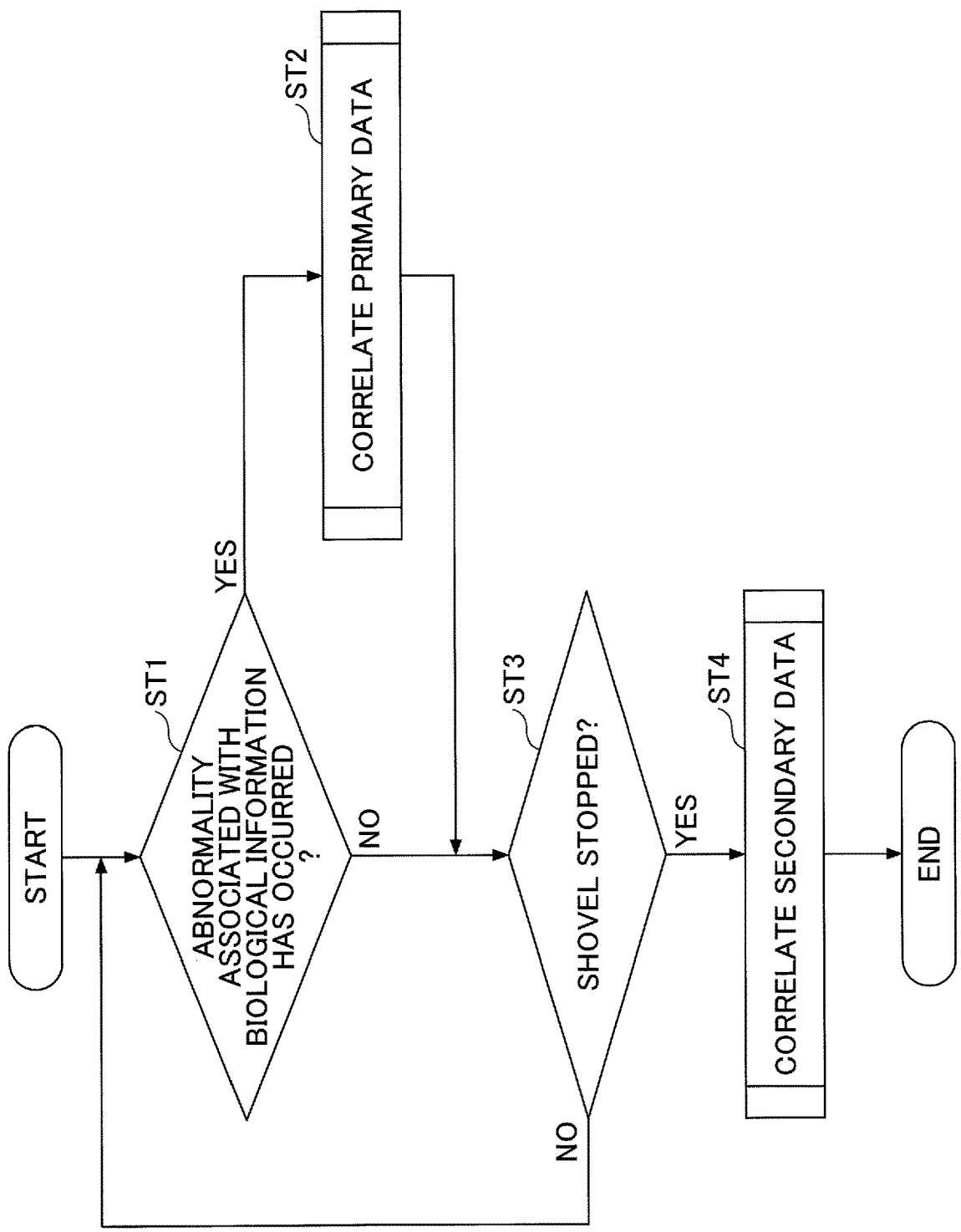
FIG. 4 is a flowchart of an example of a correlation process.

Next, a process of correlating operating information and biological information by the controller 30 (hereinafter, "correlation process") is described with reference to FIG. 4. FIG. 4 is a flowchart of an example of the correlation process. The controller 30 repeatedly executes this correlation process at predetermined control intervals while the shovel 100 is in operation. The "correlation" includes, for example, correlating operating information at a certain point of time and biological information at a corresponding point of time. Specifically, the "correlation" is performed using time information included in the operating information and time information included in the biological information. The ID number of the shovel 100, the ID number of the operator, etc., may be used.

First, the controller 30 determines whether an abnormality associated with the biological information (step ST1) has occurred. According to this embodiment, for example, the controller 30 determines that an abnormality associated with the biological information of the operator of the shovel 100 has occurred if the output of the pulse sensor S8A buried in the operator seat DS is outside a predetermined range.

In response to determining that an abnormality associated with the biological information has occurred (YES at step ST1), the controller 30 correlates primary data (step ST2).

The primary data mean unprocessed data, namely, raw data. In correlating the primary data, the controller 30 sets a point of time a predetermined time before an abnormality determination time point as a recording start time point and sets a point of time a predetermined time after the abnormality determination time point as a recording end time point. The abnormality determination time point is a point of time at which it is determined that an abnormality associated with the biological information has occurred.

Then, the controller 30 correlates the raw data of the operating information and the raw data of the biological information stored in a volatile storage medium between the recording start time point and the recording end time point, and stores them in a non-volatile storage medium as data to be analyzed. The raw data of the operating information may include an image captured by the camera S6. The controller 30 may transmit the data to be analyzed to the outside through the transmitter S1. The controller 30 may be configured to transmit the data to be analyzed to the outside at any time (for example, immediately after storage) or may be configured to transmit the data to be analyzed to the outside at a predetermined transmission time. Thereafter, the controller 30 executes step ST3.

In response to determining that no abnormality associated with the biological information has occurred (NO at step ST1), the controller 30 executes step ST3 without correlating the primary data.

At step ST3, the controller 30 determines whether the shovel is stopped. According to this embodiment, it is determined that the engine 11 is stopped when the engine key is turned to the OFF position.

In response to determining that the shovel is not stopped (NO at step ST3), the controller 30 again executes the determination of step ST1.

In response to determining that the shovel is stopped (YES at step ST3), the controller 30 correlates secondary data (step ST4). According to this embodiment, the controller 30 correlates secondary data based on the primary data stored in the volatile storage medium between a work start time and a work end time. The work start time is, for example, a time at which the engine key is turned to the ON position. The work end time is, for example, a time at which the engine key is turned to the OFF position.

The secondary data mean processed data, namely, data derived from the primary data. The secondary data include, for example, data on the work contents of the shovel. The controller 30 determines the work contents of the shovel corresponding to the last determination time at predetermined determination time intervals based on the time series data output by the operating information obtaining device S7. The work contents of the shovel are classified into, for example, "excavation work," "loading work," "standby," and "slope shaping work."

The secondary data may include statistics calculated based on the multiple primary data (raw data), such as a mean, a maximum, a minimum, a mid-range, a median, a standard deviation, and a dispersion. For example, the controller 30 may calculate a set of the statistics of the output time series data of the operating information obtaining device S7 at predetermined time (for example, a few minutes) intervals. The same applies to time series data output by the biological information obtaining device S8.

The controller 30 correlates the set of operation information-related statistics and the set of biological information-related statistics calculated at predetermined time intervals and stores them in the non-volatile storage medium as data to be analyzed. For example, the operation information-related statistics and the biological information-related statistics may be correlated with respect to each of the chronologically arranged work contents of the shovel and be stored as data to be analyzed. The same as at step ST2, the controller 30 may transmit the data to be analyzed to the outside through the transmitter S1.

Thus, in response to determining that the shovel is stopped, the controller 30 correlates the secondary data based on the primary data stored in the volatile storage medium between the work start time and the work end time. Therefore, compared with the case of correlating the primary data, the amount of data stored in the non-volatile storage medium can be reduced. The controller 30, however, may correlate the primary data at this stage as well, instead of correlating the secondary data.

Furthermore, the controller 30, which correlates the secondary data in response to determining that the shovel is stopped according to the above-described example, may correlate the secondary data at predetermined time intervals in order to address the case where the volatile storage medium is limited in capacity. The controller 30 may also correlate the secondary data in real time.

Figure 5:
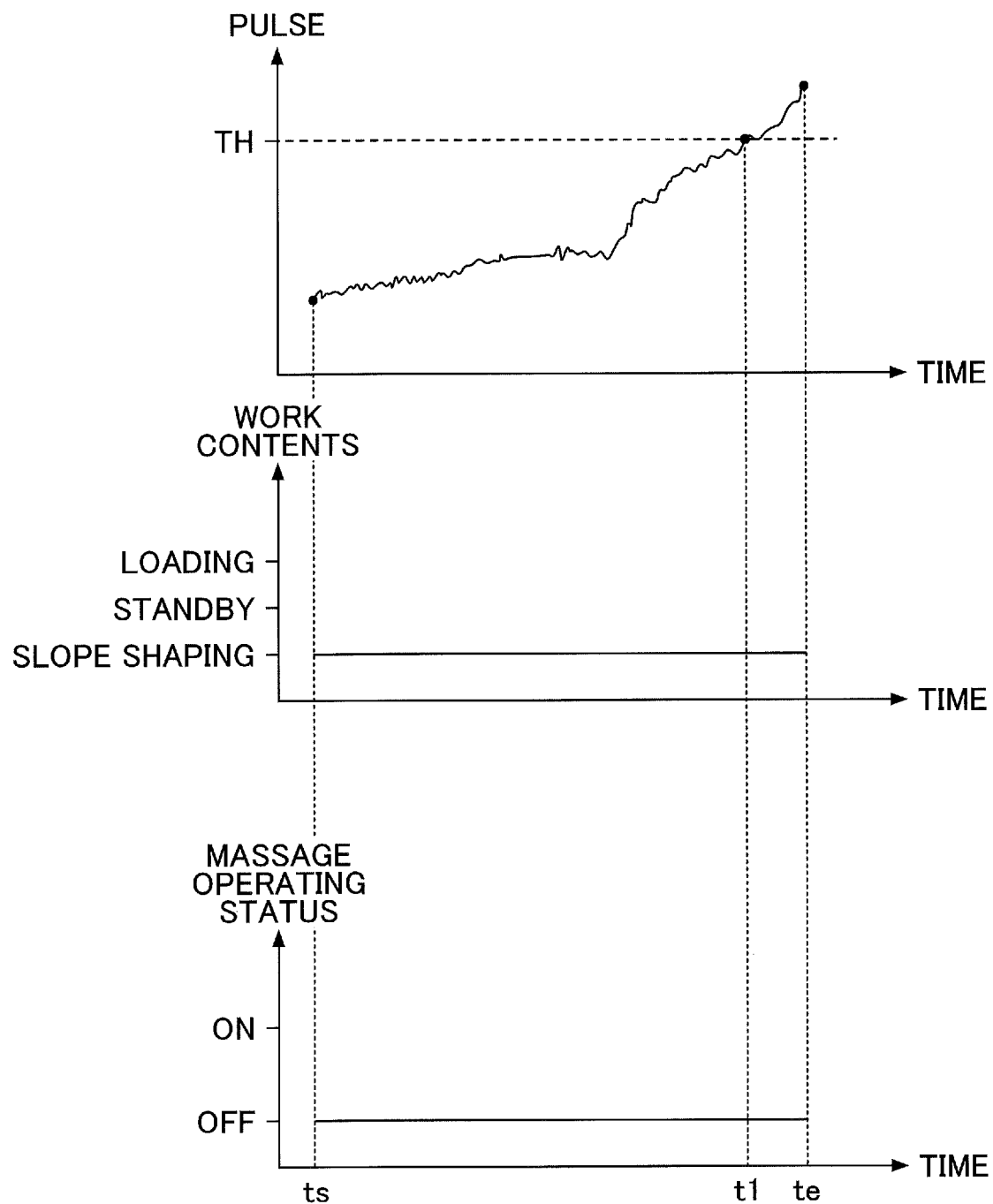
FIG. 5 is a diagram illustrating an example of information that the health management system can present.
Figure 6:
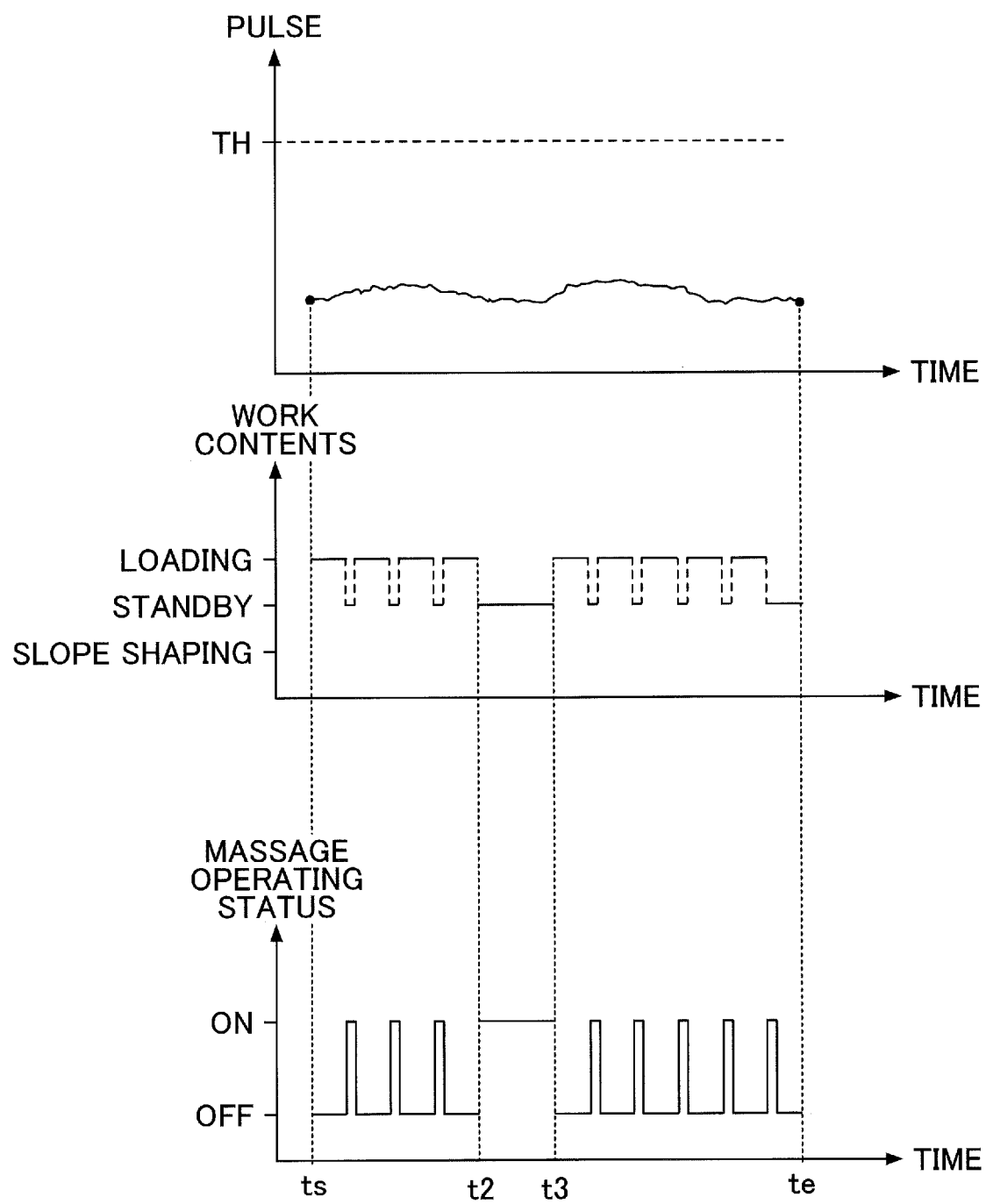
FIG. 6 is a diagram illustrating another example of the information that the health management system can present.

Next, the relationship among the biological information of the operator of the shovel 100, the operating information of the shovel 100, and the operating status of the massage function of the operator seat DS (hereinafter, "massage operating status") is described with reference to FIGS. 5 and 6. Each of FIGS. 5 and 6 illustrates an example of information that the health management system SYS can present, and specifically illustrates the relationship among a pulse as the biological information, work contents as the operating information, and the massage operating status. Each of FIGS. 5 and 6 illustrates the temporal transitions of a pulse, work contents, and the massage operating status in order from top to bottom. The temporal transition of a pulse represents the temporal transition of averages calculated at predetermined time intervals. The temporal transition of work contents represents which one of "loading," "standby," and "slope shaping" the result of determination performed at predetermined time intervals is. Furthermore, FIGS. 5 and 6 indicate that the engine key is turned on at a work start time ts and that the engine key is turned off at a work end time te. That is, FIGS. 5 and 6 indicate that a day's work starts at the work start time ts and that the day's work ends at the work end time te.

FIG. 5 illustrates that the pulse of the operator increases to exceed a threshold TH at time t1 when slope shaping work is continuously performed without a break from the work start time ts to the work end time te and the massage function is not used. The threshold TH is a value that serves as a trigger to notify the operator, a manager, or the like that the pulse of the operator is abnormal, for example.

FIG. 6 illustrates that the pulse is maintained at a level below the threshold TH when loading work is intermittently performed from the work start time ts to time t2 and is thereafter intermittently performed again from time t3 to the work end time te after a break from time t2 to time t3. Furthermore, FIG. 6 also illustrates that the massage function is used during a standby between loading operations and that the massage function is used during the break from time t2 to time t3.

In response to determining that the shovel is stopped at the work end time te, the controller 30 correlates the biological information and the operating information. According to the illustrations of FIGS. 5 and 6, the controller 30 correlates a pulse as the biological information, work contents as the operating information, and the massage operating status.

After the correlation, the controller 30 can present the relationships as illustrated in FIGS. 5 and 6 to the operator of the shovel, a manager, or the like at any time. For example, the controller 30 may display the relationships as illustrated in FIGS. 5 and 6 on the display device 40. The operator, manager, or the like receiving the presentation can understand the influence of the operating information and the massage operating status over the biological information of the operator. For example, the operator, manager, or the like can understand that the use of the massage function of the operator seat DS during the standby of the shovel 100 and during a break is effective in suppressing a pulse increase by comparing FIGS. 5 and 6.

Thus, the shovel 100 includes the operating information obtaining device S7 that obtains the operating information and the controller 30 that stores the operating information. The controller 30 is configured to obtain the biological information of the operator in the cabin 10 and correlate the biological information and the operating information. The controller 30 can present the correlated biological information and operating information to the operator or manager at any time. According to this configuration, the shovel 100 makes it possible for the operator or manager to easily manage the fatigue of the operator seated in the operator seat DS, for example. Furthermore, the shovel 100 makes it possible for the operator or manager to estimate the fatigue level of the operator with more accuracy. Furthermore, the shovel 100 can make the operator and the manager more conscious of healthcare. Furthermore, when detecting an abnormality in the biological information of the operator, the shovel 100 can immediately notify the manager to that effect.

For example, the manager can appropriately assign the next work contents by understanding the current fatigue level of the operator. That is, the manager can change a work schedule in consideration of the health and safety of the operator. For example, the manager can assign other work to the operator who has performed the same work for a long period of time. This is for reducing the fatigue of the operator.

The biological information is typically the biological information of the operator seated in the operator seat DS installed in the cabin 10. The biological information may include biological information obtained before the start of work. This is for making it possible to understand the influence of work over the biological information. Furthermore, the biological information may include biological information obtained after the end of work. This is for making it possible to understand the influence of ending work over the biological information.

The biological information is desirably obtained in such a manner as to be distinguishable between operators. This is for preventing biological information associated with an operator from being confused with biological information associated with another operator. Therefore, the indoor camera S6C, serving as an image capturing device to capture an image of the operator in the cabin 10, may be used. In this case, the operator in the cabin 10 is identified or authenticated based on the image captured by the indoor camera S6C. Furthermore, each of the assist device 200 and the management apparatus 300 may include an image capturing device such as a camera, and the operator in the cabin 10 may be identified or authenticated based on the image captured by the image capturing device of the assist device 200 or the management apparatus 300. In this case, for example, the assist device 200 or the management apparatus 300 may identify or authenticate the operator by performing various kinds of image processing on the captured image and transmit the identification or authentication result to the controller 30, or may transmit the captured image to the controller 30 and the controller 30 may identify or authenticate the operator based on the transmitted captured image. The image capturing device of the assist device 200 may be, for example, the built-in camera of a portable terminal device. The image capturing device of the management apparatus 300 may be, for example, a camera attached to a structure such as a steel tower installed in a work site and connected by wire or wirelessly to a stationary terminal apparatus installed in, for example, a management center outside the work site. Furthermore, a camera attached to an aerial vehicle such as a multicopter (drone) or an airship may be used to capture an image of the operator in the cabin 10. In this case, for example, the aerial vehicle may wirelessly transmit the captured image to the controller 30 or the management apparatus 300, and the controller 30 may identify or authenticate the operator based on the transmitted captured image or the management apparatus 300 may identify or authenticate the operator based on the transmitted captured image and transmit the identification or authentication result to the controller 30. The ID number of the operator is assigned to the biological information and the operating information.

The controller 30 may also be configured to transmit information to at least one of the assist device 200 and the management apparatus 300 for the shovel 100. For example, the controller 30 may be configured to transmit the biological information and the operating information. This is for making it possible for at least one of the assist device 200 and the management apparatus 300 to correlate the operating information and the biological information.

The biological information may be information obtained through the biological information obtaining device S8 attached to the operator seat DS installed in the cabin 10. For example, the controller 30 may be configured to obtain biological information output by the pulse sensor SBA, the body pressure sensor SBB, and the body temperature sensor S8C buried in the operator seat DS. According to this configuration, the health management system SYS can ensure that the biological information is obtained without forcing the operator to wear a wearable sensor.

Figure 7:
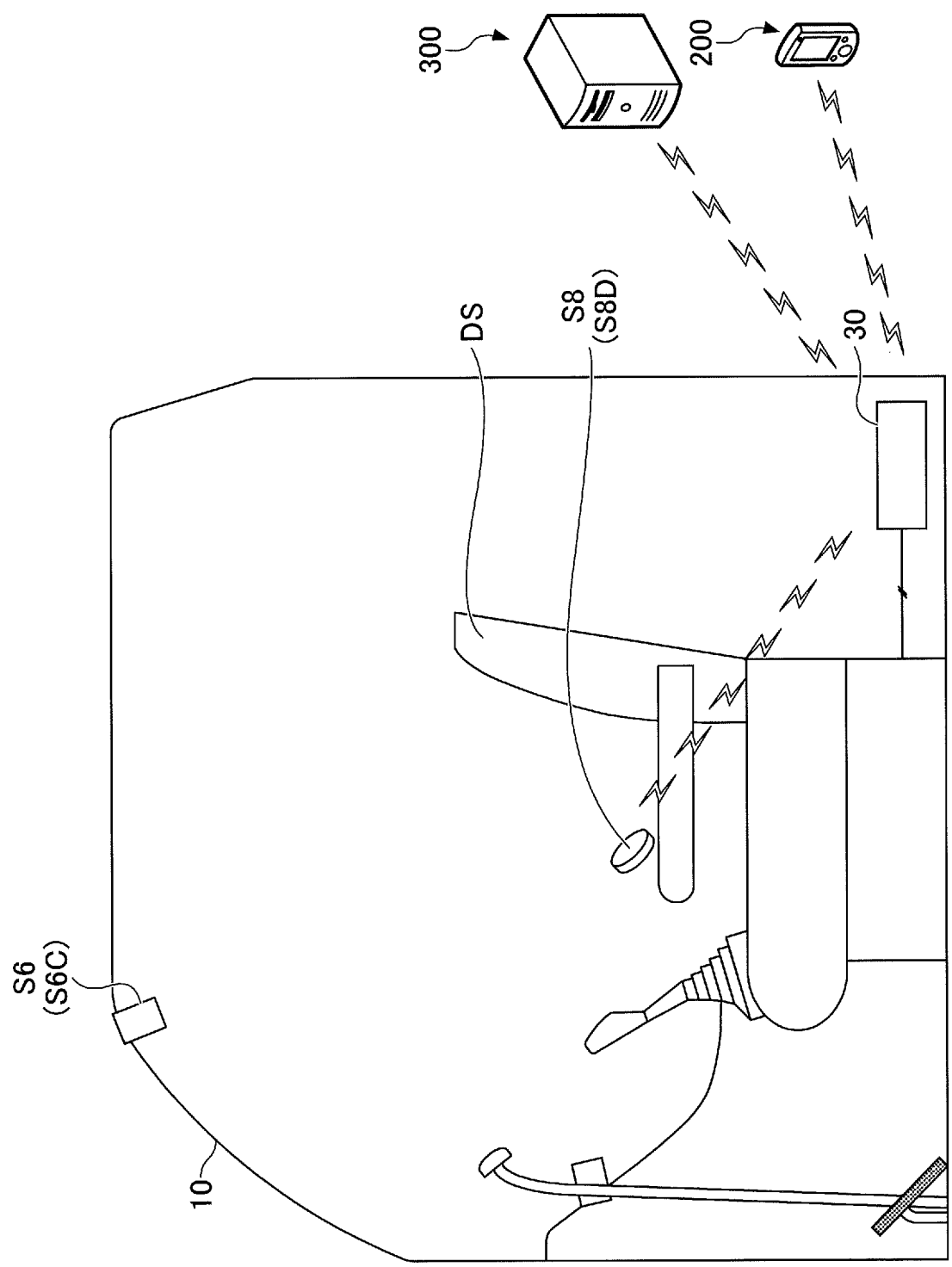
FIG. 7 is a side view of the inside of the cabin, illustrating another example configuration of the health management system.

Next, another example configuration of the health management system SYS is described with reference to FIG. 7. The health management system SYS illustrated in FIG. 7 is different in that the controller 30 correlates biological information output by a wearable sensor and the operating information and that the operator seat DS is not provided with the biological information obtaining device S8 from, but is otherwise equal to, the health management system SYS illustrated in FIG. 3. Therefore, a description of a common portion is omitted, and differences are described in detail.

According to the illustration of FIG. 7, the operator seat DS has the massage function, but is not provided with the biological information obtaining device S8 such as a pulse sensor, a body pressure sensor, or a body temperature sensor. Therefore, the controller 30 obtains biological information output by a wrist wearable pulsimeter S8D serving as a wearable sensor via wireless communications or wired communications.

For example, the controller 30 continuously obtains the biological information output by the wrist wearable pulsimeter S8D and stores it in the volatile storage medium. When the engine key is turned off, the controller 30 correlates the operating information from the work start time to the work end time stored in the volatile storage medium and the biological information. When the engine key is turned off, the controller 30 may transmit a data transmission request to the wrist wearable pulsimeter S8D. In this case, in response to the data transmission request, the wrist wearable pulsimeter S8D transmits the biological information from the work start time to the work end time to the controller 30. Thereafter, the controller 30 correlates the operating information from the work start time to the work end time stored in the volatile storage medium and the received biological information from the work start time to the work end time.

Thus, the biological information may be information obtained through the biological information obtaining device S8 worn by the operator in the cabin 10. According to this configuration, the health management system SYS can collect the biological information using a wearable sensor possessed by the operator, and therefore, does not need to prepare the dedicated biological information obtaining device S8.

Figure 8:
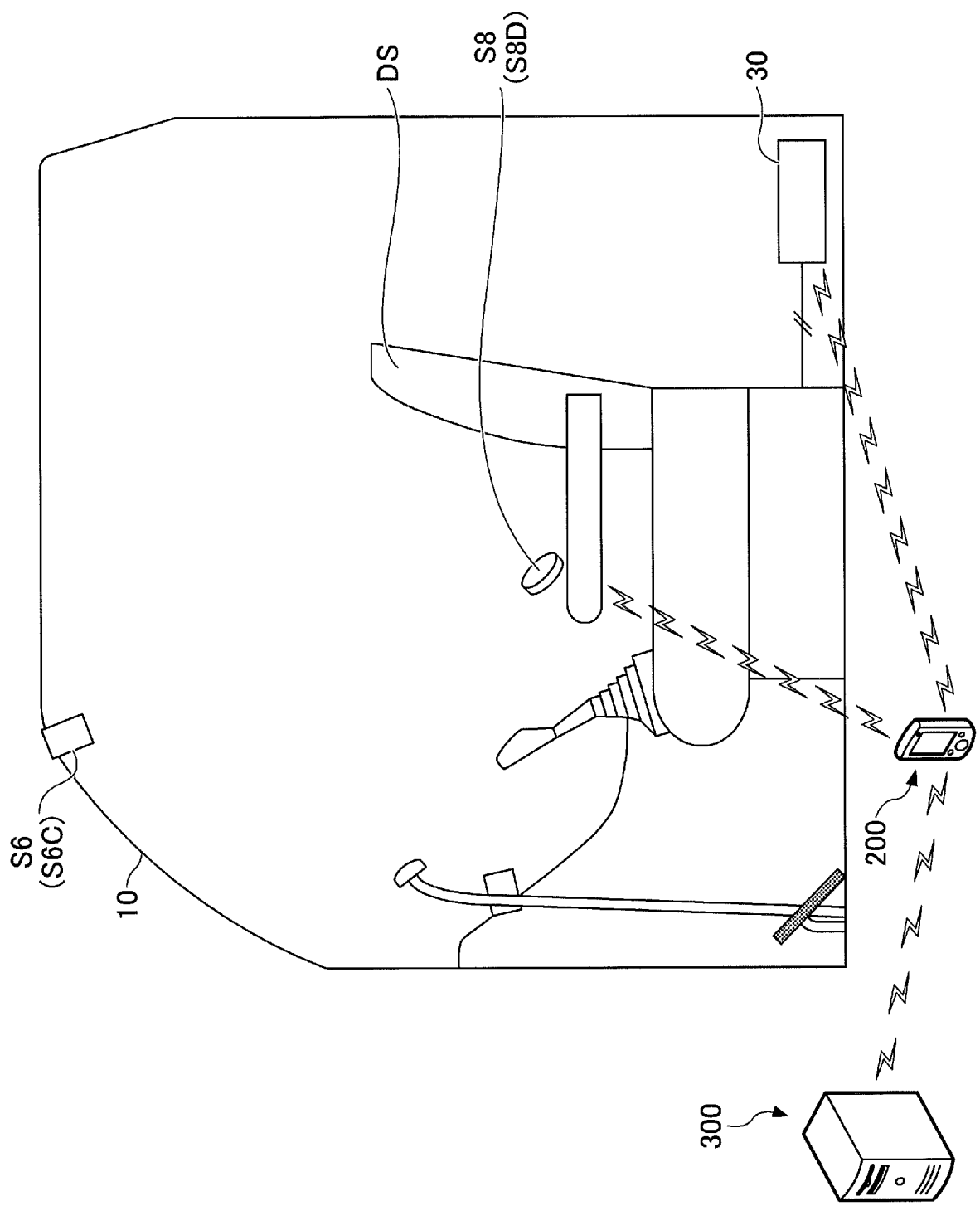
FIG. 8 is a side view of the inside of the cabin, illustrating yet another example configuration of the health management system.

Next, yet another example configuration of the health management system SYS is described with reference to FIG. 8. The health management system SYS illustrated in FIG. 8 is different in that the assist device 200 correlates the biological information and the operating information and that the operator seat DS is not provided with the biological information obtaining device S8 from, but is otherwise equal to, the health management system SYS illustrated in FIG. 3. Therefore, a description of a common portion is omitted, and differences are described in detail.

According to the illustration of FIG. 8, the operator seat DS has the massage function, but is not provided with the biological information obtaining device S8 such as a pulse sensor, a body pressure sensor, or a body temperature sensor. Therefore, the assist device 200 obtains the biological information output by the wrist wearable pulsimeter S8D serving as a wearable sensor via wireless communications. Furthermore, the assist device 200 obtains the operating information output by the controller 30 via wireless communications. The assist device 200 may obtain the biological information output by the wrist wearable pulsimeter S8D via the controller 30. In this case, the wrist wearable pulsimeter S8D transmits the biological information to the controller 30 via wireless communications or wired communications.

According to the illustration of FIG. 8, the controller 30 continuously obtains the operating information output by the operating information obtaining device S7 attached to the shovel 100 and stores it in the volatile storage medium. The assist device 200 continuously obtains the biological information output by the wrist wearable pulsimeter S8D and stores it in a volatile storage medium. When the engine key is turned off, the controller 30 transmits the operating information from the work start time to the work end time stored in the volatile storage medium to the assist device 200. In response to receiving the operating information, the assist device 200 correlates the biological information from the work start time to the work end time stored in the volatile storage medium and the received operating information from the work start time to the work end time.

When an abnormality associated with the biological information occurs, the assist device 200 may transmit a data transmission request to the controller 30. In this case, in response to the data transmission request, the controller 30 transmits the operating information from the recording start time to the recording end time to the assist device 200. Thereafter, the assist device 200 correlates the biological information from the recording start time to the recording end time stored in the volatile storage medium and the received operating information from the recording start time to the recording end time.

After the correlation, the assist device 200 can present the relationship between the biological information and the operating information to the operator of the shovel, manager, or the like at any time. For example, the assist device 200 may display the relationship between the biological information and the operating information on the display device 204. The operator, manager, or the like receiving the presentation can understand the influence of the operating information over the biological information of the operator.

Thus, the assist device 200 includes the display device 204 and the controller 201 that obtains the operating information output by the operating information obtaining device S7 attached to the shovel 100. The controller 201 is configured to obtain the biological information of the operator in the cabin 10, generate display information by correlating the biological information and the operating information, and display the display information on the display device 204. According to this configuration, for example, the assist device 200 makes it possible for the operator or manager to easily manage the fatigue of the operator seated in the operator seat DS. Furthermore, the assist device 200 makes it possible for the operator or manager to estimate the fatigue level of the operator with more accuracy. Furthermore, the assist device 200 can make the operator and the manager more conscious of healthcare.

Furthermore, when detecting an abnormality in the biological information of the operator, the assist device 200 can immediately notify the manager to that effect.

The health management system SYS may be configured such that the management apparatus 300 correlates the biological information and the operating information. In this case, the management apparatus 300 obtains the biological information output by the wrist wearable pulsimeter S8D serving as a wearable sensor via wireless communications. Furthermore, the management apparatus 300 obtains the operating information output by the controller 30 via wireless communications. The management apparatus 300 may obtain the biological information output by the wrist wearable pulsimeter S8D via the controller 30. In this case, the wrist wearable pulsimeter S8D transmits the biological information to the controller 30 via wireless communications or wired communications.

Specifically, the controller 30 continuously obtains the operating information output by the operating information obtaining device S7 attached to the shovel 100 and stores it in the volatile storage medium. The management apparatus 300 continuously obtains the biological information output by the wrist wearable pulsimeter S8D and stores it in a volatile storage medium. When the engine key is turned off, the controller 30 transmits the operating information from the work start time to the work end time stored in the volatile storage medium to the management apparatus 300. In response to receiving the operating information, the management apparatus 300 correlates the biological information from the work start time to the work end time stored in the volatile storage medium and the received operating information from the work start time to the work end time.

When an abnormality associated with the biological information occurs, the management apparatus 300 may transmit a data transmission request to the controller 30. In this case, in response to the data transmission request, the controller 30 transmits the operating information from the recording start time to the recording end time to the management apparatus 300. Thereafter, the management apparatus 300 correlates the biological information from the recording start time to the recording end time stored in the volatile storage medium and the received operating information from the recording start time to the recording end time.

After the correlation, the management apparatus 300 can present the relationship between the biological information and the operating information to the manager or the like at any time. For example, the management apparatus 300 may display the relationship between the biological information and the operating information on the display device 304. The manager or the like receiving the presentation can understand the influence of the operating information over the biological information of the operator.

Thus, the management apparatus 300 includes the display device 304 and the controller 301 that obtains the operating information output by the operating information obtaining device S7 attached to the shovel 100. The controller 301 is configured to obtain the biological information of the operator in the cabin 10, generate display information by correlating the biological information and the operating information, and display the display information on the display device 304. According to this configuration, for example, the management apparatus 300 makes it possible for the manager to easily manage the fatigue of the operator seated in the operator seat DS. Furthermore, the management apparatus 300 makes it possible for the manager to estimate the fatigue level of the operator with more accuracy. Furthermore, the management apparatus 300 can make the manager more conscious of healthcare. Furthermore, when detecting an abnormality in the biological information of the operator, the management apparatus 300 can immediately notify the manager to that effect.

Figure 9:
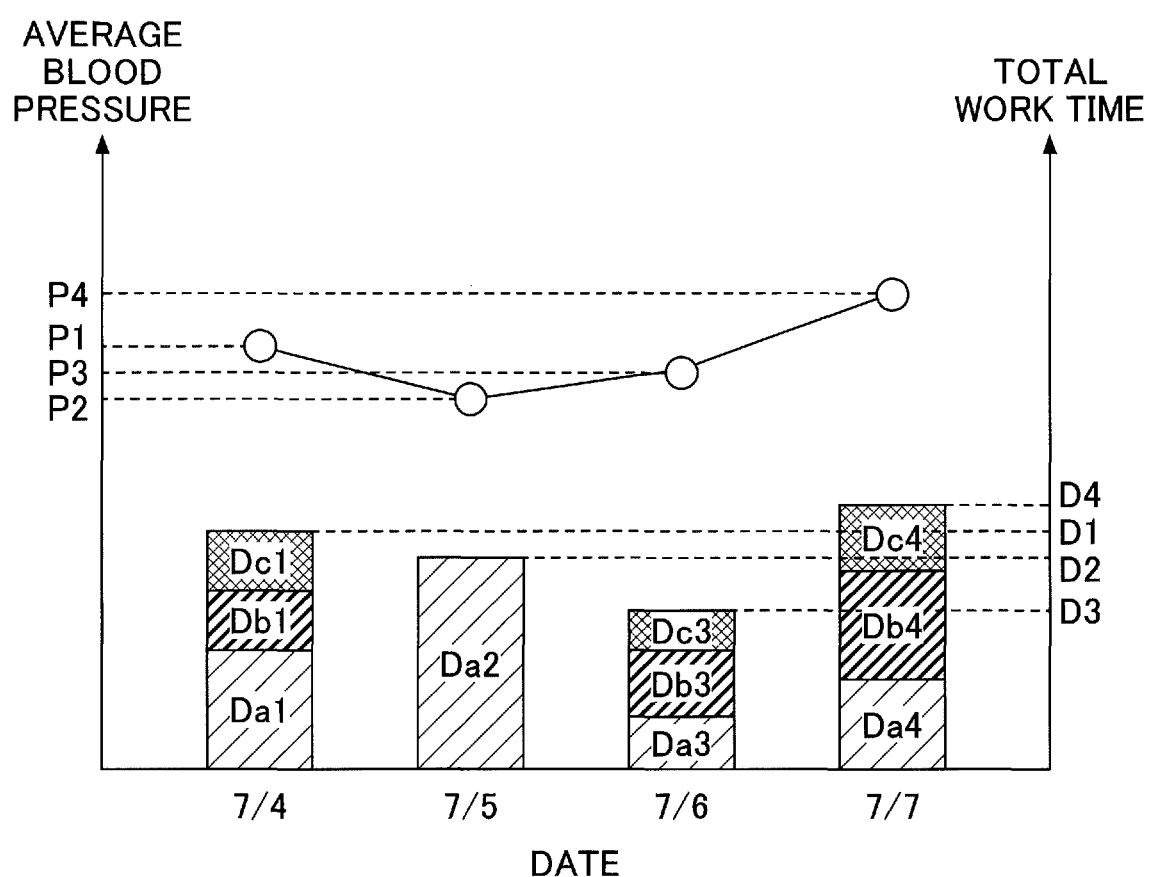
FIG. 9 is a diagram illustrating yet another example of the information that the health management system can present.

Next, another example of the information that can be presented by the health management system SYS is described with reference to FIG. 9. FIG. 9 illustrates another example of the information that the health management system SYS can present. Specifically, FIG. 9 illustrates the daily transitions of total work time and an average blood pressure. The average blood pressure represented by the left vertical axis is the average of the blood pressure of the operator of the shovel 100 repeatedly detected at predetermined intervals from the work start time to the work end time. The line graph represents the transition of the average blood pressure. The total work time represented by the right vertical axis is the time from the work start time to the work end time. The total work time is the sum of individual work times. The height of the stacked bar graph represents the total work time. Each element of the stacked bar graph represents the period of each work operation.

Specifically, FIG. 9 illustrates that the total work time of July 4 is D1 and the average blood pressure of July 4 is P1 and that the total work time D1 is the sum of a loading work time Da1, an excavation work time Db1, and a slope shaping work time Dc1. Furthermore, FIG. 9 illustrates that the total work time of July 5 is D2 and the average blood pressure of July 5 is P2 and that the total work time D2 consists only of a loading work time Da2. Furthermore, FIG. 9 illustrates that the total work time of July 6 is D3 and the average blood pressure of July 6 is P3 and that the total work time D3 is the sum of a loading work time Da1, an excavation work time Db3, and a slope shaping work time Dc3. Furthermore, FIG. 9 illustrates that the total work time of July 7 is D4 and the average blood pressure of July 7 is P4 and that the total work time D4 is the sum of a loading work time Da4, an excavation work time Db4, and a slope shaping work time Dc4.

The controller 30 can present the relationship as illustrated in FIG. 9 to the operator of the shovel, the manager, or the like at any time. Therefore, the operator of the shovel, the manager, or the like can understand the influence of work contents over the biological information of the operator, for example, can understand that the average blood pressure of the operator increases as the time of excavation work increases.

An embodiment of the present invention is described above. The present invention, however, is not limited to the above-described embodiment. Various variations, replacements, etc., may be applied to the above-described embodiment without departing from the scope of the present invention. Furthermore, the features described with reference to the above-described embodiment may be suitably combined as long as causing no technical contradiction.

What is claimed is:

1. A shovel comprising:
a lower traveling body;
an upper turning body turnably mounted on the lower traveling body;
an attachment attached to the upper turning body;
a cab mounted on the upper turning body;
an operating information obtaining device configured to obtain operating information of the shovel, the operating information including operation information of the lower traveling body, operation information of the upper turning body, and operation information of the attachment; and
a hardware processor configured to store the obtained operating information,
wherein the hardware processor is configured to
determine a work content of the shovel from among one or more work contents of the shovel based on the obtained operating information, the one or more work contents including one or more of excavation work loading work, standby, and slope shaping work, obtain biological information of an operator in the cab, the biological information including one or more of a pulse, a body temperature, and a blood pressure of the operator in the cab, detect an abnormality associated with the biological information based on the obtained biological information, and correlate the obtained biological information and the determined work content of the shovel in response to detecting the abnormality.

2. The shovel as claimed in claim 1, wherein the biological information is biological information of the operator seated in an operator seat installed in the cab.

3. The shovel as claimed in claim 1, wherein the biological information includes biological information obtained before a start of work.

4. The shovel as claimed in claim 1, wherein the biological information includes biological information obtained after an end of work.

5. The shovel as claimed in claim 1, wherein the hardware processor is configured to obtain the biological information such that the biological information is distinguishable between operators.

6. The shovel as claimed in claim 1, further comprising:
an image capturing device configured to capture an image of the operator in the cab,
wherein the operator in the cab is identified or authenticated based on the image captured by the image capturing device.

7. The shovel as claimed in claim 1, wherein the hardware processor is configured to transmit information to at least one of an assist device and a management device for the shovel.

8. The shovel as claimed in claim 1, wherein the hardware processor is configured to obtain the biological information through a biological information obtaining device worn by the operator in the cab.

9. The shovel as claimed in claim 1, wherein the hardware processor is configured to obtain the biological information through a biological information obtaining device attached to an operator seat, installed in the cab.

10. A system comprising:
a shovel including
a lower traveling body;
an upper turning body turnably mounted on the lower traveling body;
an attachment attached to the upper turning body;
a cab mounted on the upper turning body; and
an operating information obtaining device configured to obtain operating information of the shovel, the operating information including operation information of the lower traveling body, operation information of the upper turning body, and operation information of the attachment; and
an apparatus configured to assist or manage work by the shovel, the apparatus including
a hardware processor configured to obtain the operating information of the shovel and biological information of an operator in a cab of the shovel from the shovel, the biological information including one or more of, a pulse, a body temperature, and a blood pressure of the operator in the cab, determine a work content of the shovel from among one or more work contents of the shovel based on the obtained operating information, the one or more work contents including one or more of excavation work, loading work, standby, and slope shaping work, detect an abnormality associated with the biological information based on the obtained biological information, and correlate the obtained biological information of the operator and the determined work content of the shovel in response to detecting the abnormality.

11. The system as claimed in claim 10, wherein the biological information is biological information of the operator seated in an operator seat installed in the cab.

12. The system as claimed in claim 10, wherein the biological information includes biological information obtained before a start of work.

13. The system as claimed in claim 10, wherein the biological information includes biological information obtained after an end of work.

14. The system as claimed in claim 10, wherein the hardware processor is configured to obtain the biological information such that the biological information is distinguishable between operators.

15. The system as claimed in claim 10, further comprising:
an image capturing device configured to capture an image of the operator in the cab, and
the operator in the cab is identified or authenticated based on the image captured by the image capturing device.

16. The system as claimed in claim 10, wherein the hardware processor is configured to transmit information to the shovel.

17. The system as claimed in claim 10, wherein the hardware processor is configured to obtain the biological information through a biological information obtaining device worn by the operator in the cab.

18. The system as claimed in claim 10, wherein the hardware processor is configured to obtain the biological information through a biological information obtaining device attached to an operator seat installed in the cab.

19. The system as claimed in claim 10, further comprising:
a display,
wherein the hardware processor is further configured to generate display information by correlating the obtained biological information and the work content of the shovel and display the display information on the display.

* * * * *